United States Patent [19]

Aigle et al.

[11] 4,387,162

[45] Jun. 7, 1983

[54] HYBRID PLASMIDS AND MICROORGANISMS CONTAINING THEM

[75] Inventors: Michel Aigle, Illkirch-Graffemstaden; Hughes Blanc, Boulogne Billancourt; Philippe Fournier, Versailles; Claude Gerbaud, Gagny; Michel Guerineau; Henri Heslot, both of Paris; Francois Lacroute, Strasbourg, all of France

[73] Assignee: Agence Nationale de Valorisation de la Recherche (ANVAR), France

[21] Appl. No.: 94,093

[22] Filed: Nov. 14, 1979

[30] Foreign Application Priority Data

Nov. 14, 1978 [FR] France ................... 78 32100

[51] Int. Cl.[3] .................. C12N 1/16; C12N 1/18; C12N 1/20; C12N 15/00
[52] U.S. Cl. .................. 435/172; 435/68; 435/253; 435/255; 435/256; 435/317
[58] Field of Search .......... 435/172, 317, 68, 91, 435/253, 254, 255, 256

[56] References Cited

PUBLICATIONS

Petes et al., "Isolation and Analysis of Recombinant DNA Molecules Containing Yeast DNA", *Gene*, 4 (1978), 37–49.
Bolivar et al., "Constructions and Characterization of New Cloning Vehicles I. Ampicillin-Resistant Derivatives of the Plasmid pMB9", *Gene*, 2 (1977), 75–93.
Hollenberg et al., *Proc. Natl. Acad. Sci. U.S.A.*, 73(6), 2072–2076 (1976).
Hinnen et al., *Proc. Natl. Acad. Sci. U.S.A.*, 75(4), 1929–1933 (1978).
Beggs, *Nature*, 275, 104–109 (1978).
Gerbaud et al., "2 µm Plasmid Copy Number in Different Yeast Strains and Repartition of Endogeneous and 2 µm Chimeric Plasmide in Transformed Strains", *Current Genetics*, 1, 219–228 (1980).

*Primary Examiner*—Esther M. Kepplinger
*Attorney, Agent, or Firm*—Maky, Renner, Otto & Boisselle

[57] ABSTRACT

A hybrid plasmid comprising at least the DNA of a bacterial plasmid, all or part of the DNA of the 2µ plasmid of yeast and a segment of DNA including the gene $URA_3+$ of yeast. These plasmids are useful as vectors of exogenous DNA in yeasts.

10 Claims, 5 Drawing Figures

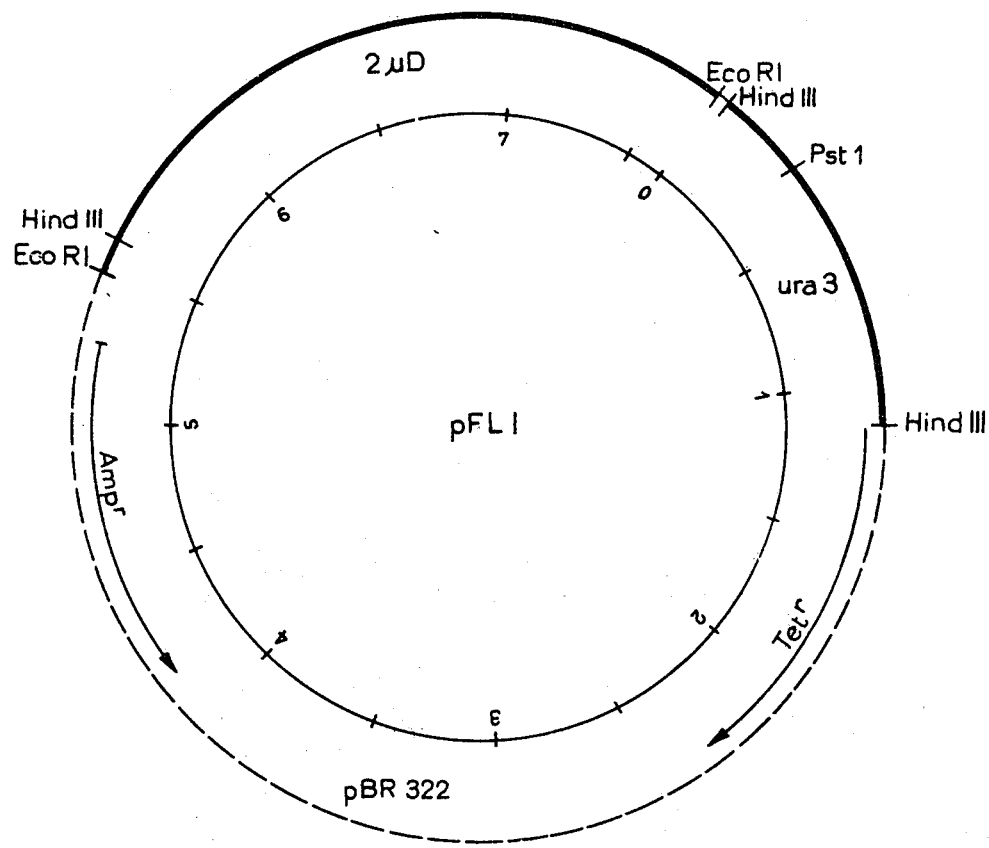
FIG_4

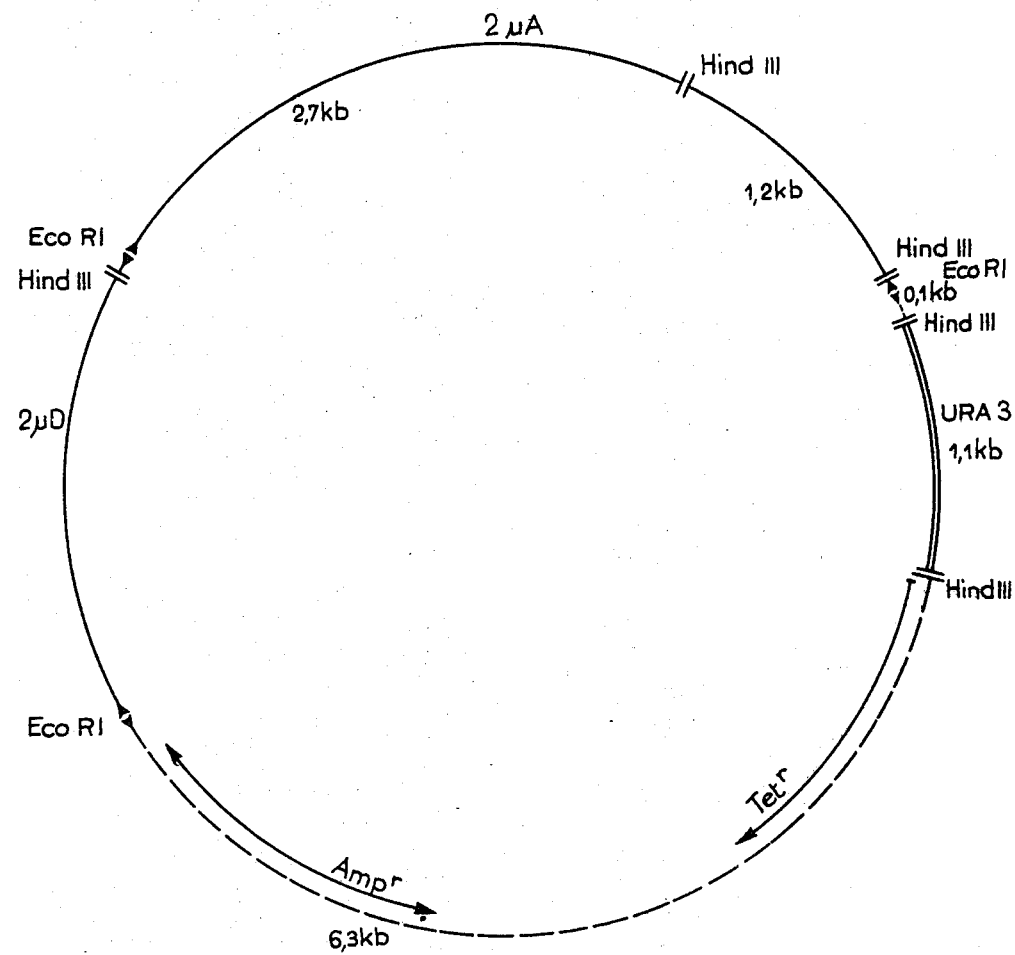
FIG_5

HYBRID PLASMIDS AND MICROORGANISMS CONTAINING THEM

TECHNICAL FIELD

The present invention relates to a new type of hybrid plasmid that is useful for modifying the properties of strains of microorganisms, particularly yeasts, and to microogramisms bearing these hybrid plasmids.

BACKGROUND OF THE INVENTION

Methods using bacterial plasmids have permitted obtaining strains of bacteria producing peptides and proteins, such as somatostatine, insulin and ovalbumin on an industrial scale. However, these bacterial systems are subject to limitations due to the differences which exist in the systems of transcription and of translation between eucaryotes and procaryotes. Moreover, a number of eucaryotes genes are discontinuous and have insertions (up to 7 for chicken ovalbumin). Consequently, such genes cannot be properly translated by a procaryote, unless a gene without insertions is constructed.

Yeasts which are eucaryote microorganisms offer the possibility of removing these constraints, and thus have great potential interest for many practical applications.

However, until recently, it was not known how to effect the entry of an exogenous deoxribonucleic acid (DNA) into yeast, cause it to remain there in stable form and express itself. The work of A. Hinnen, J. B. Hicks and G. R. Finck, Proc. Natl. Acad. Sci. USA (1978), 75, 1929–33, discloses that by using a bacterial plasmid vector bearing the gene $LEU_2^+$ of yeast, clones of yeasts are obtained that have integrated all or part of the vector without, however, the latter being maintained autonomously in the cytoplasm. This method has the disadvantage, however, of not permitting the amplification of the original exogenous DNA.

It is known, that certain bacterial plasmids exist in multiple-copy state in the bacteria which bear them and it is also known that there exists in certain yeast strains, particularly Saccharomyces cerevisiae, a plasmid designated as $2\mu$ because of its length. This $2\mu$ plasmid exists at the level of about 50 to 100 copies per cell and while its precise genetic function is not known, it is known that it can be transcribed, at least in part, and, consequently, can constitute a vector of potentially great interest.

SUMMARY OF THE INVENTION

An object of the present invention is to provide plasmidic vectors for introducing a particular gene into a microorganism, and more particularly, into a yeast. An advantage of the present invention is that the particular gene, so introduced, is stable, can express itself and can be amplified.

In accordance with the present invention, there is provided means which permits transforming the properties of a microorganism, particularly yeast, in a predetermined way that is superior to known mutation techniques. The present invention contemplates the provision of a hybrid plasmid comprising a DNA of a bacterial plasmid, all or part of the DNA of the $2\mu$ plasmid of yeast, and a segment of a yeast DNA that includes the gene $URA_3^+$.

BRIEF DESCRIPTION OF THE DRAWINGS

To facilitate understanding the method of the present invention, certain of the plasmids used in this method are represented in the attached figures, in which

FIG. 4 represents the scheme of the DNA of the plasmid pFL 1; and

FIG. 5 represents the scheme of the DNA of the plasmid pMA 1.

DESCRIPTION OF THE PREFERRED EMBODIMENTS

The $2\mu$ plasmid of yeast is known. A complete study may be found in "Viruses and Plasmid in Fungi", editor Paul A. Lemki; this work may also be used as a reference for the meaning of certain terms of which the complete definition is not given in the present specification.

The gene $URA_3^+$ is the coding gene for orotidine-5'-phosphate-decarboxylase; in its absence, yeast can only develop in a medium containing uracil. The presence or absence of this gene permits the "screening" of yeasts using mediums with and without uracil.

In a preferred embodiment of the present invention, the segment of DNA containing the gene $URA_3^+$ of yeast is inserted in the DNA of the $2\mu$ plasmid of yeast, preferably between the sites of Hind III (1) and Hind III (3) restriction, with loss of the corresponding segment of the DNA of the $2\mu$ plasmid of yeast.

The sites of Hind III restriction correspond to places on the DNA molecule which are cleaved by a particular enzyme, the Hind III endonuclease (hereinafter Hind III). These Hind III restriction sites are three in number on the $2\mu$ plasmid and are called Hind III (1), Hind III (2) and Hind III (3) (hereinafter H1, H2 and H3).

In another preferred embodiment of the present invention, the DNA segment including the gene $URA_3^+$ of yeast, is inserted into the DNA of the bacterial plasmid. Among the DNA's of bacterial plasmid which may be used, there is the DNA of the plasmid pCR1 and the plasmid pBR 322 (Bethesda Research Laboratory Inc., in Rockville, Maryland).

In a particularly advantageous embodiment of the present invention, the DNA of the bacterial plasmid includes the insertion of an exogenous DNA from a procaryote or, preferably, a eucaryote organism, such as a yeast. Hybrid plasmids in which the $2\mu$ plasmid includes an insertion of an exogenous DNA from a procaryote or, preferably a eucaryote organism are also provided.

The vector plasmids according to the present invention may be prepared by known techniques. Described hereinafter is a general method for the preparation of two particularly useful plasmids in accordance with the present invention.

Figure 1:
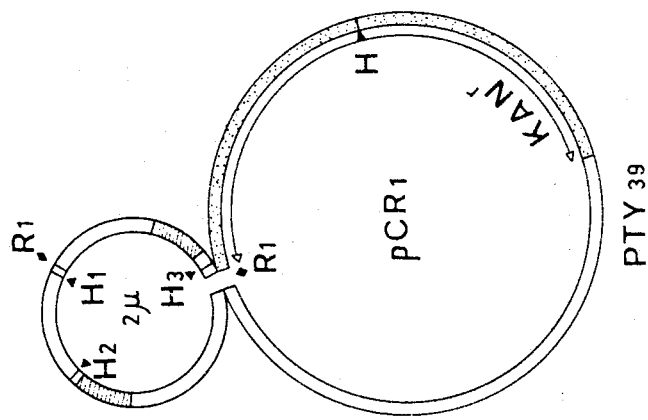
FIG. 1 represents the scheme of the DNA of the plasmid PTY 39.

Hybrid plasmid PTY 39 is described in the article of Hollenberg et al., *Proc. Nat. Acad. Sci.*, USA, 73, 2072–2076, (1976). This plasmid is represented in FIG. 1.

The plasmid PTY consists of two sequences:

—The DNA of the $2\mu$ plasmid of yeast, and

—The bacterial plasmid on pCR1, on which is indicated by an arcuate arrow and by the letters KAN$^r$ the gene of the plasmid which permits giving it the character of resistance to kanamycin.

The DNA fragment corresponding to the plasmid pCR1 has only one Hind III restriction site, designated by H and situated in the gene KAN$^r$. The DNA of the 2$\mu$ plasmid of PTY 39 includes, on the other hand, three Hind III restriction sites, numbered H1, H2 and H3, an Eco R1 restriction site, marked R1, between H1 and H3, and Eco R1 junction restriction sites. The presence of these Eco R1 restriction sites means that the DNA is cleaved at this level by the endonuclease Eco R1. It is important to note that the Eco R1 restriction site is located between the restriction sites H1 and H3. The shaded elements of the DNA of the 2$\mu$ plasmid locate the sequences repeated in reverse. This hybrid plasmid PTY 39 is grown and harvested by treating the bacterium which is the bearer of the same with chloroamphenicol.

The second hybrid plasmid is pMB 9—URA$_3$+. This hybrid plasmid consists of a bacterial plasmid pMB 9, in which has been inserted a DNA fragment of yeast, bearing the gene URA$_3$+, between two Hind III restriction sites. First, a partial digestion of the plasmid PTY 39 by the Hind III endonuclease is effected. Then a complete digestion of the plasmid pMB 9—URA$_3$+, by the same enzyme, is followed by a separation of the restriction fragments by electrophoresis. A fragment of 1.1 kilobase, bearing the gene URA$_3$+, is isolated. The partially digested plasmid PTY 39 is mixed with the fragment bearing the gene URA$_3$+, previously isolated, in the presence of ligase. The pyrF bacteria (that is, those involved in the gene of the orotidine-5'-phosphate-decarboxylase) are then transformed by the DNA obtained after ligation in the preceding step. The clones developing on minimum medium, which are the Escherichia coli pyr+ and which have integrated the plasmids bearing the gene URA$_3$+, are then selected.

From these Escherichia coli pyr+ are separated the clones sensitive to kanamycin; thus two types of strains are obtained:

*Escherichia coli* pyr+ Kan$^r$ and
*Escherichia coli* pyr+ KAN$^s$.

From these two types of strains are extracted two types of plasmid, according to the invention:

—the plasmid G 9, which gives the phenotype pyr+ Kan$^r$

—and the plasmid G 18 which gives the phenotype pyr+ Kan$^s$.

Figure 3:
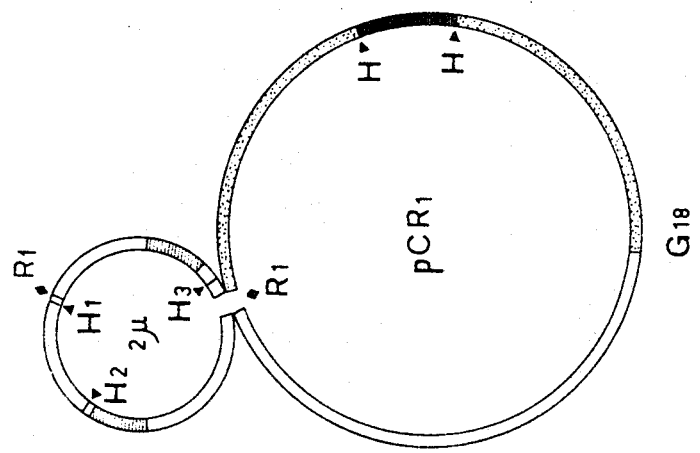
FIG. 3 represents the scheme of the DNA of the plasmid G 18.
Figure 2:
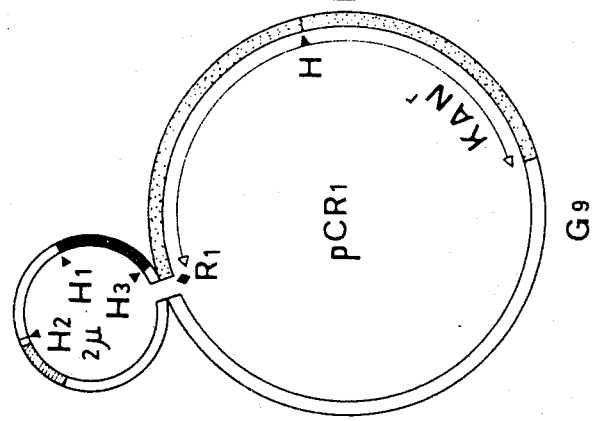
FIG. 2 represents the scheme of the DNA of the plasmid G 9.

The plasmids G 9 and G 18 are represented in FIGS. 2 and 3, respectively.

The plasmid G 9 includes a part of bacterial DNA from pCR 1, which is identical with that which was found in PTY 39. As for the DNA part from yeast, there is represented a heavy line (FIG. 2) indicating the segment of DNA, which is the bearer of the gene URA$_3$+, and which is fixed between the H1 and H3 restriction sites with a corresponding loss of the 2$\mu$ plasmid segment.

It is important to note that replacing the DNA segment of the 2$\mu$ plasmid, situated between the restriction sites H1 and H3, by the DNA of yeast bearing the gene URA$_3$+, results in the disappearance of the Eco R1 restriction site. This restriction site originally was in the DNA of the 2$\mu$ plasmid between the sites H1 and H3.

The plasmid G 18 includes all of the DNA of the 2$\mu$ plasmid. The PTY 39, on the other hand, which is the fragment of bacterial DNA from pCR1, includes the insertion, at the level of the Hind III restriction site, of the fragment of DNA bearing the gene URA$_3$+, represented by the heavy line (FIG. 3).

The hybrid plasmids G 9 and G 18, so obtained, may be maintained in situ, or in a yeast, or a bacterium, where they will multiply and may be extracted as desired.

These plasmids may be introduced into a yeast by the following method. A strain of yeast, Saccharomyces cerevisiae URA$_3$−, for example, is used. This strain has the advantage of a low rate of reversion. This strain, which is cultivated in a complete medium, is harvested in exponential phase.

The cells are transformed into protoplasts by digestion of the walls with the aid of helicase in the presence of an osmotic stabilizer. The protoplasts are placed in the presence of the DNA of the hybrid plasmid G 9 or G 18 for about 10 minutes, then mixed with polyethylene glycol at 30% and allowed to stand for about 15 minutes. The mixture is centrifuged. The residue from the centrifuge is put in suspension in a medium containing an osmotic stabilizer. Incubation is permitted for 1 hour at 30° C., followed by a second centrifuging. The residue is then suspended again in a hypertonic medium containing agar (3%), which is maintained in superfusion at 44% C., and 0.03% yeast extract. The resulting mixture is poured into Petri dishes.

For the purposes of comparison, control yeasts are treated in the same way, but without adding DNA of hybrid plasmid. At the end of 3 to 5 days, many colonies appear on the dishes corresponding to the cells treated with DNA, while there are none on the control dishes.

The colonies so obtained are called "transformants" (TRA) and consist of microorganisms which can function as a source of hybrid plasmid G 9 or G 18 and as messengers, particularly for the preparation of orotidine-5'-phosphate-decarboxylase. The enzyme activity of orotidine-5'-phosphate-decarboxylase in the autonomous strain URA$_3$+ is on the order of about two units. On the other hand, a number of transformants, that is strains prepared in accordance with the present invention, exhibit such enzyme activity on the order of about 10 to about 35 units.

It is believed that the function of each of the different fragments of the plasmids according to the present invention is as follows:

—The URA$_3$+fragment permits "screening" of the microorganisms treated with the plasmids of the invention;

—The 2$\mu$ fragment permits the amplifying of the properties transferred by the plasmids of the invention.

The plasmids of the present invention may thus be employed in the production of orotidine-5'-phosphate-decarboxylase, which is a product used in enzymatic industries.

An advantage of the hybrid plasmids according to the present invention, particularly the hybrid plasmids G 9 and G 18, is that they can be transformed so as to serve as vectors for the introduction of exogenous DNA into microorganisms which, after transformation, also are part of the present invention. It should be noted that the hybrid plasmid G 9 has no Eco R1 restriction sites except at the junction between the yeast DNA and the bacterial DNA and, consequently, the action by the endonuclease Eco R1 leads to the separation of the yeast DNA and the bacterial DNA. This separation makes it possible to attract at the Eco R1 site of the yeast DNA, a new bacterial DNA bearing, for example, an exogenous DNA.

The hybrid plasma G 18 has the advantage of possessing a DNA of complete 2μ plasmid, which permits replication and maintenance in a yeast strain, for example, more certain than in the case of the plasmid G 9 due to the fact that with the plasmid G 9, the DNA of the 2μ plasmid has been cleaved of a segment between the restriction sites H1 and H3. The plasmid G 18 has two Eco R1 restriction sites which, during the action of the corresponding enzyme may lead to a more complicated fractioning of the DNA than in the case of G 9 and, consequently, make the introduction of bacterial DNA bearing an exogenous DNA more difficult.

The examples which follow are designed to illustrate a method of preparation of hybrid plasmids and of microorganisms according to the present invention. It is to be understood, however, that these examples are not to be considered as limiting the scope of the invention.

EXAMPLE 1

Preparation of the Plasmids G 9 and G 18

A pMB9—$URA_3^+$ plasmid is prepared by the method disclosed in T. D. Petes et al, Gene, Vol. IV, 1978, p. 37–49, by digesting the DNA of an autonomous yeast of Saccharomyces cerevisiae by means of the Hind III endonuclease, and at the same time digesting the plasmid pMB 9, Bolivar et al, Gene 2, 75–93 (1977), with the same enzyme. The two products of digestion are ligated by the ligase DNA T 4. The sorting of the plasmids obtained is effected by using a strain of Escherichia coli $URA_3^-$, which is transformed by these plasmids which are the only ones to grow on a minimum medium, without uracil. The pMB 9—$URA_3^+$ plasmids of the selected Escherichia coli $URA_3^+$ are extracted.

Twenty micrograms of the product of digestion of the pMB 9—$URA_3^+$ plasmid by the Hind III endonuclease (supplied by Boehringer) are subjected to an electrophoresis on an agarose gel at 1%.

The fragment of 1.1 kilobase, bearing the gene $URA_3^+$ of yeast is recovered from the gel by the so-called "Freeze and Squeeze" method (Thuring, 1975) and by precipitation with ethanol.

The circular DNA of the plasmid PTY 39 is partly digested by the Hind III endonuclease, to obtain a majority of molecules that include a single cleavage. After heating at 60° C. for 10 minutes to inactivate the enzyme, and after dialysis, 1 microgram of the digested DNA of PTY 39 is mixed with about 0.05 microgram of the fragment of 1.1 kilobase, bearing the gene $URA_3^+$ of yeast. The two fragments are added to the DNA T 4 ligase to a volume of 50 microliters for 3 minutes at 37° C., then for 5 hours at 10° C.

The ligation mixture (50 microliters) is diluted with 900 microliters of a buffer containing 10 mM of Tris pH 7, 10 mM of $CaCl_2$, 10 mM of $MgSO_4$. One-hundred microliters of this dilute mixture are added to 200 microliters of Escherichia coli $URA_3^-$ cells, prepared for transformation by the method of Cohen et al (1975). The transformation mixture is left on ice for 25 minutes, then subjected for 3 minutes to a pulsed heating to 37° C., then lift at room temperature for 10 minutes. One ml of complete medium is then added and the mixture is agitated at 37° C. for one hour. The cells are collected by centrifuging and then spread on a minimum medium.

The $URA_3^+$ clones obtained are then selected, taking account of their resistance to kanamycin.

In this way the clones of Escherichia coli, which are bearers of G 9 and which resist kanamycin, are selected. Similarly, the clones of Escherichia coli, which are bearers of G 18 and which do not resist kanamycin, are selected. The plasmids G 9 and G 18 are then extracted.

EXAMPLE 2

Preparation of Yeasts

The yeast strains, which are receivers of $URA_3^-$, are prepared by cultivating them on 500 milliliters of complete medium, until a cellular density of about $2 \times 10^7$ cells per milliliter is reached. The cells are washed in 300 ml of distilled water and in 300 ml of 1.2 M sorbitol. The cells are then placed in suspension in 50 ml of a mixture of 1.2 M sorbitol, 0.05 M phosphate-citrate at a pH of 5.8 and helicase (supplied by the Industre Biologique Francais) which is added until a final concentration of 6,500 units per ml has been reached. The cells are incubated at 28° C. for one hour, to one hour and 30 minutes, under light agitation. During the incubation, the formation of spheroplasts is followed by known optical techniques.

The spheroplasts are washed by centrifuging at room temperature and then placed in again three times suspension in 150 ml of 1.2 M sorbitol, 10 mM of Tris at a pH of 7.6, and 10 mM of $CaCl_2$. The spheroplasts are concentrated in the same buffer until a cellular density of about $10^9$ cells per milliliter is reached. The DNA of plasmid obtained previously in 10 mM $CaCl_2$ and 10 mM Tris at a pH of 6 (about 10 microliters) is mixed with 0.2 ml of spheroplasts until a concentration of 5 to 15 micrograms per ml is reached. The mixture is allowed to stand at room temperature for 10 minutes, and then 2 ml of Tris, 10 mM $CaCl_2$ and 4000 grams of polyethylene glycol at 30% are added. After mixing, the mixture is allowed to stand for 15 minutes at room temperature. The spheroplasts are recovered by centrifuging 2500 grams of the mixture for 10 minutes, placing the mixture in suspension in a medium containing 1.2 M sorbitol, 4 grams per liter yeast extract, 6 grams per liter glucose, 6 grams per liter bactopeptone Difco, 10 mM of $CaCl_2$ and 10 mM Tris at a pH of 6, which is agitated lightly for one hour at 28° C.

The mixture is centrifuged, then placed in suspension again in 0.2 ml of the preceding buffer. The samples are mixed with 8 ml gelose (1.2 M sorbitol, 20 grams per liter of glucose, 0.8 grams per liter bactotryptone Difco, 0.3 grams per liter yeast extract, 30 grams per liter of purified gelose Difco) at 44° C., and poured into the same medium with the exception of the concentration in gelose, which is 20 grams per liter.

The dilutions are spread by the same method in the same media, supplemented with 50 micrograms per liter uracil, so as to measure the effectiveness of the regeneration of the spheroplasts.

The results obtained are listed in Table I.

TABLE I

| DNA | Run No. | Number of Cells per Dish | Number of Cells Regenerated | Percentage of Regeneration | Number of $URA^+$ Clones | Frequency of Transformation Per Viable Cell |
|---|---|---|---|---|---|---|
| G 18 | 1 | $2.4 \times 10^8$ | $6.4 \times 10^7$ | 26.7 | 1000 | $1.5 \times 10^{-5}$ |
|  | 2 | $5.3 \times 10^6$ | $1.7 \times 10^5$ | 3.2 | 18 | $1.0 \times 10^{-4}$ |
| G 9 | 1 | $2.4 \times 10^8$ | $6.4 \times 10^7$ | 26.7 | 1500 | $2.3 \times 10^{-5}$ |

TABLE I-continued

| DNA | Run No. | Number of Cells per Dish | Number of Cells Regenerated | Percentage of Regeneration | Number of URA+ Clones | Frequency of Transformation Per Viable Cell |
|---|---|---|---|---|---|---|
| | 2 | $5.3 \times 10^6$ | $1.7 \times 10^5$ | 3.2 | 30 | $1.8 \times 10^{-4}$ |
| None | 1 | $2.4 \times 10^8$ | $6.4 \times 10^7$ | 26.7 | 0 | |
| | 2 | $5.3 \times 10^6$ | $1.7 \times 10^5$ | 3.2 | 0 | |

EXAMPLE 3

Study of the Activity of the Yeasts Obtained

The activity of orotidine-5'-phosphate-decarboxylase is measured by obtaining cells in logarithmic growth phase on minimum medium and preparing a crude extract by the method of Lacroute (1962).

The enzymatic test is conducted according to Beckwith et al (1962), except that $MgCl_2$ is omitted from the reaction mixture. The proteins are measured by the method of Lowry et al (1951), lysozyme being used as the standard.

The results obtained are listed in Table II.

The TRA (Transformants) strains are strains obtained in Example 2.

The specific activity for orotidine-5'-phosphate-decarboxylase is expressed in moles of decarboxylated substratum per minute and per milligram of protein.

The increase of specific activity indicates the ratio between the specific activity of the TRA's after correction for the specific activity of the autonomous strain.

TABLE II

| Plasmids | Strains | Specific Activity | Percentage of Protrophes in the Culture | Corrected Specific Activity | Increase of Specific Activity |
|---|---|---|---|---|---|
| None | Autonomous Strain | 2 | 100 | 2 | 1 |
| G 9 | TRA$_1$ | 35 | 46 | 76 | 38 |
| | TRA$_2$ | 21 | 52 | 40 | 20 |
| | TRA$_3$ | 33 | 44 | 75 | 38 |
| G 18 | TRA 363 | 15 | 67 | 22 | 11 |
| | TRA 366 | 10 | 43 | 23 | 12 |
| | TRA 367 | 22 | 81 | 27 | 14 |

EXAMPLE 4

Similarly to Examples 1 and 2, a plasmid pBR 322 is prepared, with the fragment bearing the gene URA$_3$+ inserted at the level of the Hind III site. The partial digestion of the plasmid obtained, by the enzyme Eco R1, is effected. The partial digestion of the 2μ plasmid of the strain of S. cerevisiae FL 100 ATCC 28383, by the enzyme Eco R1, is effected. The two digestion products are mixed, after inhibition of the enzyme Eco R1, and the fragments of the mixture are joined, with the ligase, for one night at 10° C. The plasmids obtained are extracted and a receiver URA$_3$ strain of S. cerevisiae yeast, is transformed; that is the plasmids not being able to grow without uracil are extracted and the transformants which can grow on medium without uracil are selected. From these transformants, URA$_3$+ plasmids are extracted which can, as has been described, be used to transform a strain E. coli ura$_3$− which, by selection of the strain URA$_3$+ obtained, constitutes a reservoir of plasmids of which the structure is given in FIGS. 4 and 5.

FIG. 4 represents the plasmid pFL 1 (represented by the dotted lines) which includes the DNA of the plasmid pBR 322 with the insertion of the DNA of the gene URA$_3$+ (represented by the double line) at the level of the Hind III iste of the DNA of pBR 322 of a fragment of the DNA of the 2μ plasmid, the fragment 2 μD (fragment defined in relation to the Eco R1 sites).

Three other plasmids are isolated: pFL 2, pFL 3 and pFl 4. For pFL 2, the DNA of the gene URA$_3$+ has the reverse orientation; that is, the site Pst 1 is at 0.8 kb from the Eco R1 site taken as origin. The plasmids pFL 3 and pFL 4 have the 2 μD fragment in reverse orientation from that observed for pFL 1 and pFL 2, respectively. The total length of this plasmid is 7.652 kb.

The plasmid pBR 322 bears a gene of resistance to ampicilline (Amp$^r$), which gene codes for a penicillinase. In a yeast transformed by a plasmid of this type (such as pFL 1 or pFL 2), this bacterial gene is expressed and an excretion of penicillinase by transformed yeasts is identified. This shows the advantage of the plasmids of the present invention for use in the extraction of proteins, particularly enzymes.

Another advantage of the plasmids of the present invention is that they demonstrate that the integrity of the 2μ plasmid is not indispensable to its replication and its maintenance in yeast. The advantage of this construction is that it permits providing for the cloning of foreign DNA fragments of large sizes, since the receiving plasmid is smaller. Plasmids of too large a size are more fragile, and more difficult to handle and to extract from bacteria or yeasts.

In the same way, the plasmid pMA 1, represented in FIG. 5, is obtained. This plasmid has the same structure as the preceding plasmid, but has the integrity of the DNA of the 2μ (2μ A +2μ D) plasmid instead of the 2μ D fragment.

Plasmids similar to those described above have been used (see Panthier, J. J. et al, Comptes Rendu Acad. Sciences, Serie D, 1979, Session of October 29) by inserting therein the DNA of the gene lacZ of E. coli, in order to transform a strain of S. cerevisiae. There is observed in the transformed yeast the presence of a galactosidase which is absent from the original strain. This permits one to conclude that the bacterial gene lacZ is expressed from the yeast.

What is claimed is:

1. A hybrid plasmid comprising a DNA of a bacterial plasmid, all or part of the DNA of a 2μ plasmid of yeast, and a DNA segment of about 1.1 kb including the gene URA$_3$+ of yeast which is limited by two Hind III restriction sites.

2. A hybrid plasmid according to claim 1, wherein the DNA segment, including the gene URA$_3$+ of yeast, is inserted in the DNA of the 2μ plasmid of yeast.

3. A hybrid plasmid according to claim 2, wherein the DNA segment including the gene URA$_3$+ of yeast, is inserted in the DNA of the 2μ plasmid of yeast, between the restriction sites Hind III (1) and Hind III (3), with corresponding loss of segment of the DNA of the 2μ plasmid of yeast.

4. A hybrid plasmid according to claim 1, wherein the DNA segment including the gene URA$_3$+ of yeast is inserted in the DNA of the bacterial plasmid.

5. A hybrid plasma according to claim 2 wherein the DNA of the bacterial plasmid includes an insertion of a DNA of a eucaryote organism.

6. A hybrid plasmid according to claim 4, wherein the DNA of the bacterial plasmid includes the insertion of a DNA of a eucaryote organism as well as the DNA segment including the gene $URA_3^+$ of yeast.

7. A hybrid plasmid according to claim 1 wherein the DNA of bacterial plasmid is the DNA of the plasmid pCR1 or pBR 322.

8. A plasmid according to claim 1 wherein the DNA of the 2μ plasmid of yeast is inserted in the DNA of the bacterial plasmid between the Eco R1 restrictions sites.

9. A microorganism including a hybrid plasmid according to any of claims 1 to 8.

10. A yeast according to claim 9.

* * * * *